US007608082B2

(12) United States Patent  (10) Patent No.: US 7,608,082 B2
Cuevas et al.                (45) Date of Patent:     Oct. 27, 2009

(54) SURGICAL SEAL FOR USE IN A SURGICAL ACCESS APPARATUS

(75) Inventors: Brian Cuevas, Middletown, CT (US); Thomas Wenchell, Durham, CT (US); Frank J. Viola, Sandy Hook, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 728 days.

(21) Appl. No.: 11/030,634

(22) Filed: Jan. 6, 2005

(65) Prior Publication Data

US 2006/0149305 A1    Jul. 6, 2006

(51) Int. Cl.
*A61F 11/00* (2006.01)
(52) U.S. Cl. .................................................. 606/108
(58) Field of Classification Search ................. 606/108; 604/167.06, 158, 164.01, 164.02, 167.01, 604/264
See application file for complete search history.

(56) References Cited

U.S. PATENT DOCUMENTS

| 4,007,909 | A |   | 2/1977  | Buseth et al.     |
|-----------|---|---|---------|-------------------|
| 4,126,133 | A |   | 11/1978 | Schwartz          |
| 4,473,211 | A |   | 9/1984  | Fremy             |
| 4,475,548 | A | * | 10/1984 | Muto ..... 128/207.14 |
| 4,586,694 | A |   | 5/1986  | Jones             |
| 4,665,752 | A |   | 5/1987  | Huschelrath et al.|
| 4,686,977 | A |   | 8/1987  | Cosma             |
| 4,874,378 | A |   | 10/1989 | Hillstead         |
| 4,917,668 | A |   | 4/1990  | Haindl            |
| 4,929,235 | A |   | 5/1990  | Merry et al.      |
| 4,960,412 | A |   | 10/1990 | Fink              |
| 5,123,634 | A |   | 6/1992  | Schwerdt          |
| 5,127,626 | A |   | 7/1992  | Hilal et al.      |
| 5,197,955 | A |   | 3/1993  | Stephens et al.   |

(Continued)

FOREIGN PATENT DOCUMENTS

EP    0 567 141    10/1993

(Continued)

OTHER PUBLICATIONS

European Search Report.

(Continued)

*Primary Examiner*—(Jackie) Tan-Uyen T. Ho
*Assistant Examiner*—Gregory A Anderson (57) ABSTRACT

A seal assembly for use with an access apparatus during a surgical procedure includes a housing defining a longitudinal axis and having a passageway dimensioned to permit passage of an object. The housing is adapted for mounting to a surgical access apparatus and has internal wall portions defining an internal chamber. A seal is mounted within the internal chamber of the housing and is adapted to form a substantial sealing relation with the object. The seal is mounted for reciprocal movement within the internal chamber in a general transverse direction to the longitudinal axis. A viscous fluid is disposed within the internal chamber surrounding the seal and is adapted to form a substantial seal between the seal and the internal wall portions of the housing. The fluid may have lubricious characteristic to facilitate sliding movement of the seal relative to the internal wall portions of the housing. Alternatively, the fluid includes a therapeutic agent or a pharmacological agent which is released to treat the underlying tissue. A foam material may be disposed within the internal chamber. The foam material is at least partially saturated with the fluid.

14 Claims, 5 Drawing Sheets

U.S. PATENT DOCUMENTS

| | | | |
|---|---|---|---|
| 5,201,714 | A | 4/1993 | Gentelia et al. |
| 5,209,736 | A | 5/1993 | Stephens et al. |
| 5,209,737 | A | 5/1993 | Ritchart et al. |
| 5,211,633 | A | 5/1993 | Stouder, Jr. |
| 5,221,264 | A | 6/1993 | Wilk et al. |
| 5,224,930 | A | 7/1993 | Spaeth et al. |
| 5,242,412 | A | 9/1993 | Blake, III |
| 5,251,873 | A | 10/1993 | Atkinson et al. |
| 5,273,545 | A | 12/1993 | Hunt et al. |
| 5,295,657 | A | 3/1994 | Atkinson |
| 5,300,033 | A | 4/1994 | Miller |
| 5,300,035 | A | 4/1994 | Clement |
| 5,308,336 | A | 5/1994 | Hart et al. |
| 5,330,436 | A | 7/1994 | Heidmueller |
| 5,338,307 | A | 8/1994 | Stephens et al. |
| 5,342,315 | A | 8/1994 | Rowe et al. |
| 5,350,362 | A | 9/1994 | Stouder, Jr. |
| 5,366,446 | A | 11/1994 | Tal et al. |
| 5,380,288 | A | 1/1995 | Hart et al. |
| 5,385,553 | A | 1/1995 | Hart et al. |
| 5,389,080 | A | 2/1995 | Yoon |
| 5,389,081 | A | 2/1995 | Castro |
| 5,391,153 | A | 2/1995 | Haber et al. |
| 5,395,342 | A | 3/1995 | Yoon |
| 5,397,335 | A | 3/1995 | Gresl et al. |
| 5,403,284 | A | 4/1995 | Gross |
| 5,405,330 | A | 4/1995 | Zunitch et al. |
| 5,407,433 | A | 4/1995 | Loomas |
| 5,411,483 | A | 5/1995 | Loomas et al. |
| 5,423,761 | A | 6/1995 | Hein et al. |
| 5,460,616 | A * | 10/1995 | Weinstein et al. ...... 604/167.03 |
| 5,476,475 | A | 12/1995 | Gadberry |
| 5,478,318 | A | 12/1995 | Yoon |
| 5,492,304 | A | 2/1996 | Smith et al. |
| 5,496,280 | A | 3/1996 | Vandenbroek et al. |
| 5,509,643 | A | 4/1996 | Carstens et al. |
| 5,512,053 | A | 4/1996 | Pearson et al. |
| 5,514,133 | A | 5/1996 | Golub et al. |
| 5,531,758 | A | 7/1996 | Uschold et al. |
| 5,540,661 | A | 7/1996 | Tomisaka et al. |
| 5,545,142 | A | 8/1996 | Stephens et al. |
| 5,554,124 | A | 9/1996 | Alvarado |
| 5,569,205 | A | 10/1996 | Hart et al. |
| 5,569,206 | A | 10/1996 | Gorman, Jr. et al. |
| 5,584,850 | A | 12/1996 | Hart et al. |
| 5,603,702 | A | 2/1997 | Smith et al. |
| 5,607,397 | A | 3/1997 | Stephens et al. |
| 5,613,663 | A | 3/1997 | Schmidt et al. |
| 5,628,732 | A | 5/1997 | Antoon, Jr. et al. |
| 5,634,908 | A | 6/1997 | Loomas |
| 5,657,963 | A | 8/1997 | Hinchliffe et al. |
| 5,662,615 | A | 9/1997 | Blake, III |
| 5,676,657 | A | 10/1997 | Yoon |
| 5,709,664 | A | 1/1998 | Vandenbroek et al. |
| 5,720,759 | A | 2/1998 | Green et al. |
| 5,752,938 | A | 5/1998 | Flatland et al. |
| 5,755,702 | A | 5/1998 | Hillstead et al. |
| 5,779,697 | A | 7/1998 | Glowa et al. |
| 5,782,817 | A | 7/1998 | Franzel et al. |
| 5,792,113 | A | 8/1998 | Kramer et al. |
| 5,820,600 | A | 10/1998 | Carlson et al. |
| 5,820,604 | A | 10/1998 | Fox et al. |
| 5,820,606 | A | 10/1998 | Davis et al. |
| 5,827,228 | A | 10/1998 | Rowe |
| 5,865,817 | A | 2/1999 | Moenning et al. |
| 5,868,714 | A | 2/1999 | Danks |
| 5,871,471 | A | 2/1999 | Ryan et al. |
| 5,879,368 | A | 3/1999 | Hoskin et al. |
| 5,895,377 | A | 4/1999 | Smith et al. |
| 5,906,595 | A | 5/1999 | Powell et al. |
| 5,989,224 | A | 11/1999 | Exline et al. |
| 5,989,233 | A | 11/1999 | Yoon |
| 5,993,471 | A | 11/1999 | Riza et al. |
| 6,000,670 | A | 12/1999 | Okamoto |
| 6,030,403 | A | 2/2000 | Long et al. |
| RE36,702 | E | 5/2000 | Green et al. |
| 6,066,117 | A | 5/2000 | Fox et al. |
| 6,068,011 | A | 5/2000 | Paradis |
| 6,077,249 | A | 6/2000 | Dittrich et al. |
| 6,077,288 | A | 6/2000 | Shimomura et al. |
| 6,083,203 | A | 7/2000 | Yoon |
| 6,093,176 | A | 7/2000 | Dennis |
| 6,110,154 | A | 8/2000 | Shimomura et al. |
| 6,123,689 | A | 9/2000 | To et al. |
| 6,159,182 | A | 12/2000 | Davis et al. |
| 6,176,843 | B1 | 1/2001 | DiCaprio et al. |
| 6,197,002 | B1 | 3/2001 | Peterson |
| 6,217,555 | B1 | 4/2001 | Hart et al. |
| D449,887 | S | 10/2001 | Haberland et al. |
| 6,482,181 | B1 | 11/2002 | Racenet et al. |
| 6,551,282 | B1 | 4/2003 | Exline et al. |
| 6,595,946 | B1 | 7/2003 | Pasqualucci |
| 6,702,787 | B2 | 3/2004 | Racenet et al. |
| 2002/0156432 | A1 | 10/2002 | Racenet et al. |
| 2003/0139756 | A1 | 7/2003 | Brustad |
| 2003/0172941 | A1 | 9/2003 | Streifenger et al. |
| 2004/0106942 | A1 | 6/2004 | Taylor et al. |

OTHER PUBLICATIONS

European Search Report for corresponding European Patent Application—EP07023424—Date of Mailing Mar. 6, 2008 (4 pages).

* cited by examiner

FIG. 6

SURGICAL SEAL FOR USE IN A SURGICAL ACCESS APPARATUS

BACKGROUND

1. Field of the Disclosure

The present disclosure relates to surgical devices and, more particularly, to a seal assembly for use with a surgical access apparatus during a minimally invasive surgical procedure.

2. Description of the Related Art

Minimally invasive surgical procedures including both endoscopic and laparoscopic procedures permit surgery to be performed on organs, tissues and vessels far removed from an opening within the tissue. Laparoscopic and endoscopic procedures generally require that any instrumentation inserted into the body be sealed, i.e. provisions must be made to ensure that gases do not enter or exit the body through the incision as, for example, in surgical procedures in which the surgical region is insufflated. These procedures typically employ surgical instruments which are introduced into the body through a cannula. The cannula has a seal assembly associated therewith. The seal assembly provides a substantially fluid tight seal about the instrument to preserve the integrity of the established pneumoperitoneum.

SUMMARY

The present disclosure is directed to further improvements in seal assemblies for use with access devices during a surgical procedure. In one preferred embodiment, the seal assembly includes a housing defining a longitudinal axis and having a passageway dimensioned to permit passage of an object. The housing is adapted for mounting to a surgical access apparatus and has wall portions defining an internal chamber. A seal is mounted within the internal chamber of the housing and is adapted to form a substantial sealing relation with the object. The seal is mounted for reciprocal movement within the internal chamber in a general transverse direction to the longitudinal axis. A viscous fluid is disposed within the internal chamber surrounding the seal and is adapted to form a substantial seal between the seal and the wall portions of the housing. In one preferred embodiment, the seal comprises an outer annular support collar and an inner seal portion defining an opening for permitting passage of the object. Preferably, the fluid has a lubricious characteristic to facilitate sliding movement of the annular support collar relative to the wall portions of the housing.

In one preferred embodiment, the wall portions of the housing are dimensioned to permit seepage of the fluid from the internal chamber into the passageway. In this embodiment, the fluid comprises a therapeutic agent or a pharmacological agent including, e.g., a medicinal, wound treatment agent, antibiotic, antiseptic, growth factor or an anti-inflammatory agent.

In an alternative embodiment, a foam material is disposed within the internal chamber. The fluid is disposed within the foam material and/or the foam material may be at least partially saturated with the fluid.

In another preferred embodiment, a surgical access apparatus is provided. The access apparatus includes a housing member having wall portions defining an internal chamber and an access member mounted to the housing member. The access member defines a longitudinal axis and has a longitudinal opening dimensioned for passage of an object. A seal member is disposed within the internal chamber of the housing member and is adapted to traverse the internal chamber upon manipulation of the object. The seal member includes a peripheral portion and an inner seal portion extending radially inwardly from the peripheral portion. The inner seal portion is adapted to permit passage of the object in substantial sealed relation therewith. A foam material is disposed within the internal chamber surrounding the peripheral portion of the seal member. The foam material comprises a viscous fluid adapted to form a fluid tight seal between the peripheral portion of the seal member and the wall portions of the housing. The foam material may comprise a lubricant to facilitate sliding movement of the peripheral portion of the seal member relative to the wall portions of the housing. Alternatively, the foam material may include a pharmacological agent or a therapeutic agent. The wall portions are desirably dimensioned so as to permit seepage of the fluid from the internal chamber.

The inner seal portion of the seal member may include a central aperture for reception of the object. A zero closure valve may be included in the surgical access apparatus so that the zero closure valve closes in the absence of the object. The surgical access apparatus desirably includes a housing comprising a cannula housing and an access member comprising a cannula sleeve.

In another preferred embodiment, a surgical access apparatus includes an access member dimensioned to access underlying tissue and defines a longitudinal axis. The access member has wall portions defining an internal chamber and a longitudinal opening dimensioned for passage of an object. A seal is mounted within the internal chamber of the access member and is adapted to form a substantial sealing relation with the object. The seal is mounted for reciprocal movement within the internal chamber in a general transverse direction to the longitudinal axis. A fluid is disposed within the internal chamber surrounding the seal. The fluid comprises one of a pharmacological agent or therapeutic agent. Desirably, the fluid is released into the passageway to communicate with the underlying tissue. The wall portions of the housing may be dimensioned to permit seepage of the fluid from the internal chamber and into the passageway to communicate with the underlying tissue. Preferably, a foam material is disposed within the internal chamber wherein the fluid is contained within the foam material.

BRIEF DESCRIPTION OF THE DRAWING(S)

Preferred embodiments of the present disclosure will be better appreciated by reference to the drawings wherein.

DETAILED DESCRIPTION OF THE PREFERRED EMBODIMENT(S)

The seal assembly of the present disclosure, either alone or in combination with a seal system internal to a cannula assembly, provides a substantial seal between a body cavity of a patient and the outside atmosphere before, during and after insertion of an object through the cannula assembly. Moreover, the seal assembly of the present invention is capable of accommodating objects of varying diameters, e.g., instruments from about 4.5 mm to about 15 mm, by providing a gas tight seal with each instrument when inserted. The flexibility of the present seal assembly greatly facilitates endoscopic surgery where a variety of instruments having differing diameters are often needed during a single surgical procedure.

The seal assembly contemplates the introduction and manipulation of various types of instrumentation adapted for insertion through a trocar and/or cannula assembly while maintaining a fluid tight interface about the instrumentation to prevent gas and/or fluid leakage from the established pneumoperitoneum so as to preserve the atmospheric integrity of a surgical procedure. Specifically, the seal assembly accommodates angular manipulation of the surgical instrument relative to the seal axis. This feature of the present disclosure desirably minimizes the entry and exit of gases and/or fluids to/from the body cavity. Examples of instrumentation include clip appliers, graspers, dissectors, retractors, staplers, laser probes, photographic devices, endoscopes and laparoscopes, tubes, and the like. Such instruments will be collectively referred to herein as "instruments or instrumentation".

The seal assembly may be readily incorporated into an access device, such as a conventional trocar device or cannula, and provides the device with sealing capability about an inserted instrument. The seal assembly is also adapted to emit or release therapeutic or pharmacological agents during use, which agents communicate to the underlying tissue to provide desired therapeutic effects on the tissue. Example agents include antimicrobial, antibacterial, hemostatic, moisture-providing agents, such as saline, healing agents, lubricious agents, antiseptics, growth factors, and/or anti-inflammatory agents.

The seal assembly may also be adapted to receive and form a seal about a physician's arm or hand during a hand-assisted laparoscopic procedure. In this application, the seal assembly is a component of an access member which is introduced within the body to provide access to underlying tissue in, e.g., the abdominal cavity.

Figures 1, 2:
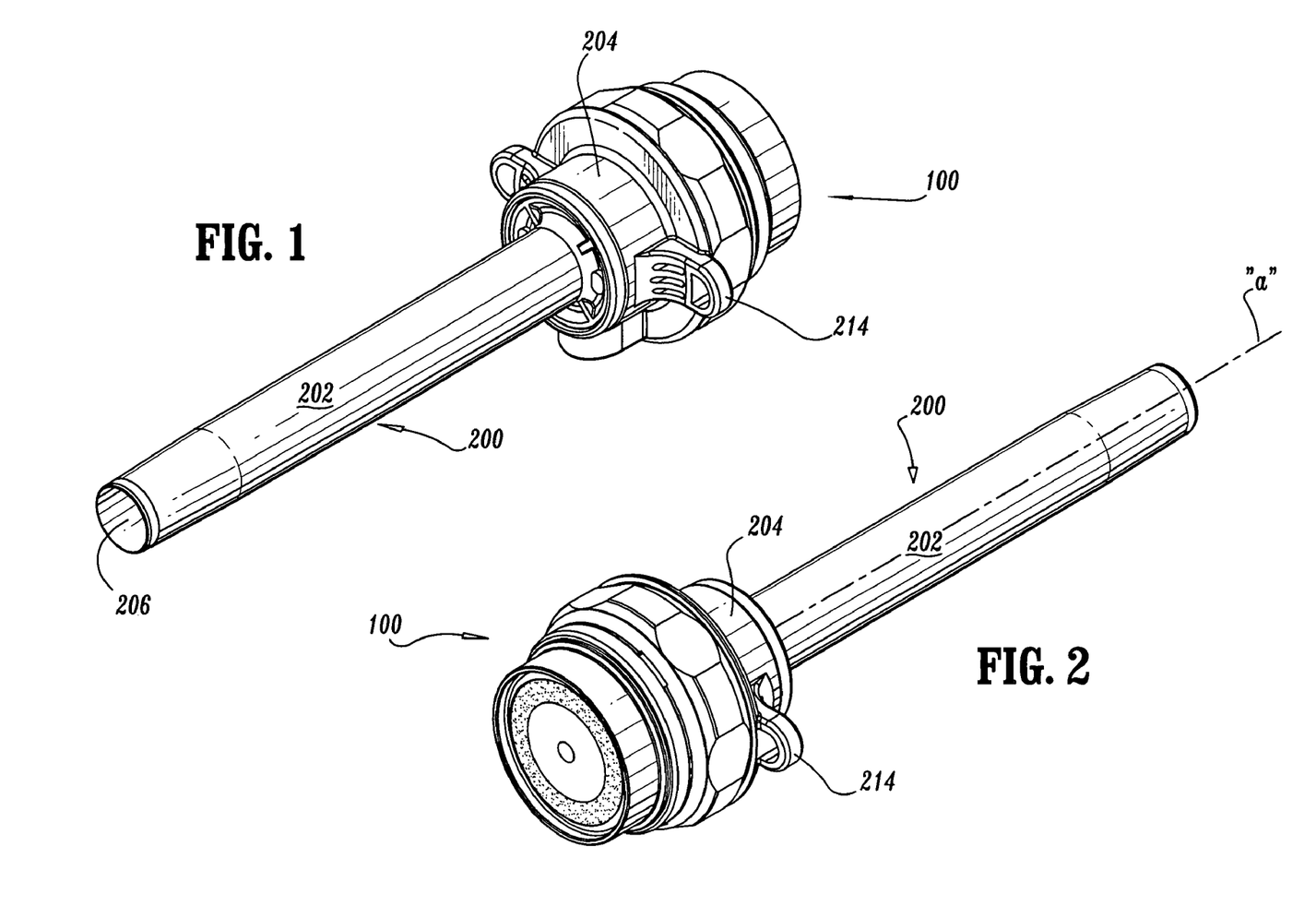
FIGS. 1-2 are perspective views of a cannula assembly and a seal assembly in accordance with the principles of the present disclosure.

Referring now to the drawings, in which like reference numerals identify identical or substantially similar parts throughout the several views, FIGS. 1-2 illustrate the seal assembly 100 of the present disclosure mounted to an access device such as cannula assembly 200. Cannula assembly 200 may be any member suitable for the intended purpose of accessing a body cavity and typically defines a passageway permitting introduction of instruments therethrough. Cannula assembly 200 is particularly adapted for use in laparoscopic surgery where the peritoneal cavity is insufflated with a suitable gas, e.g., $CO_2$, to raise the cavity wall from the internal organs therein. Cannula assembly 200 is typically used with an obturator assembly (not shown) which may be blunt, a non-bladed, or a sharp pointed instrument positionable within the passageway of the cannula assembly 200. The obturator assembly is utilized to penetrate the abdominal wall or introduce the cannula assembly 200 through the abdominal wall, and then subsequently is removed from the cannula assembly 200 to permit introduction of the surgical instrumentation utilized to perform the procedure through the passageway.

Cannula assembly 200 includes cannula sleeve 202 and cannula housing 204 mounted to a proximal end of the cannula sleeve 202. Cannula sleeve 202 defines a longitudinal axis "a" extending along the length of the cannula sleeve 202. Cannula sleeve 202 further defines an internal longitudinal passage 206 dimensioned to permit passage of surgical instrumentation. Cannula sleeve 202 may be formed of any suitable medical grade material, such as stainless steel or other rigid materials, including polymeric materials, such as polycarbonate, or the like. Cannula sleeve 202 may be transparent or opaque. The diameter of cannula sleeve 202 may vary, but typically ranges from about 4.5 to about 15 mm.

Figure 3:
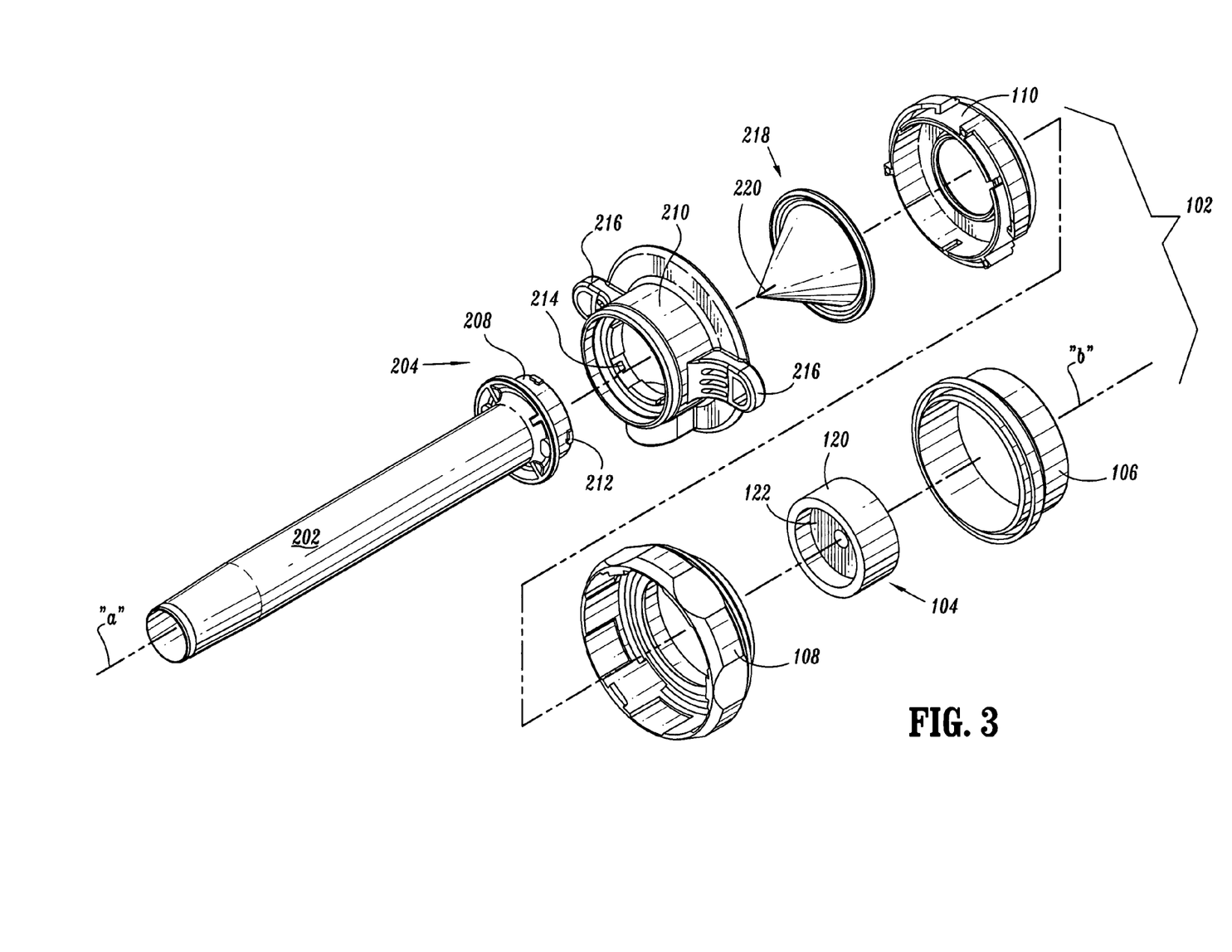
FIG. 3 is a perspective view with parts separated of the cannula and seal assemblies in accordance with the embodiment of FIGS. 1-2.
Figure 4:
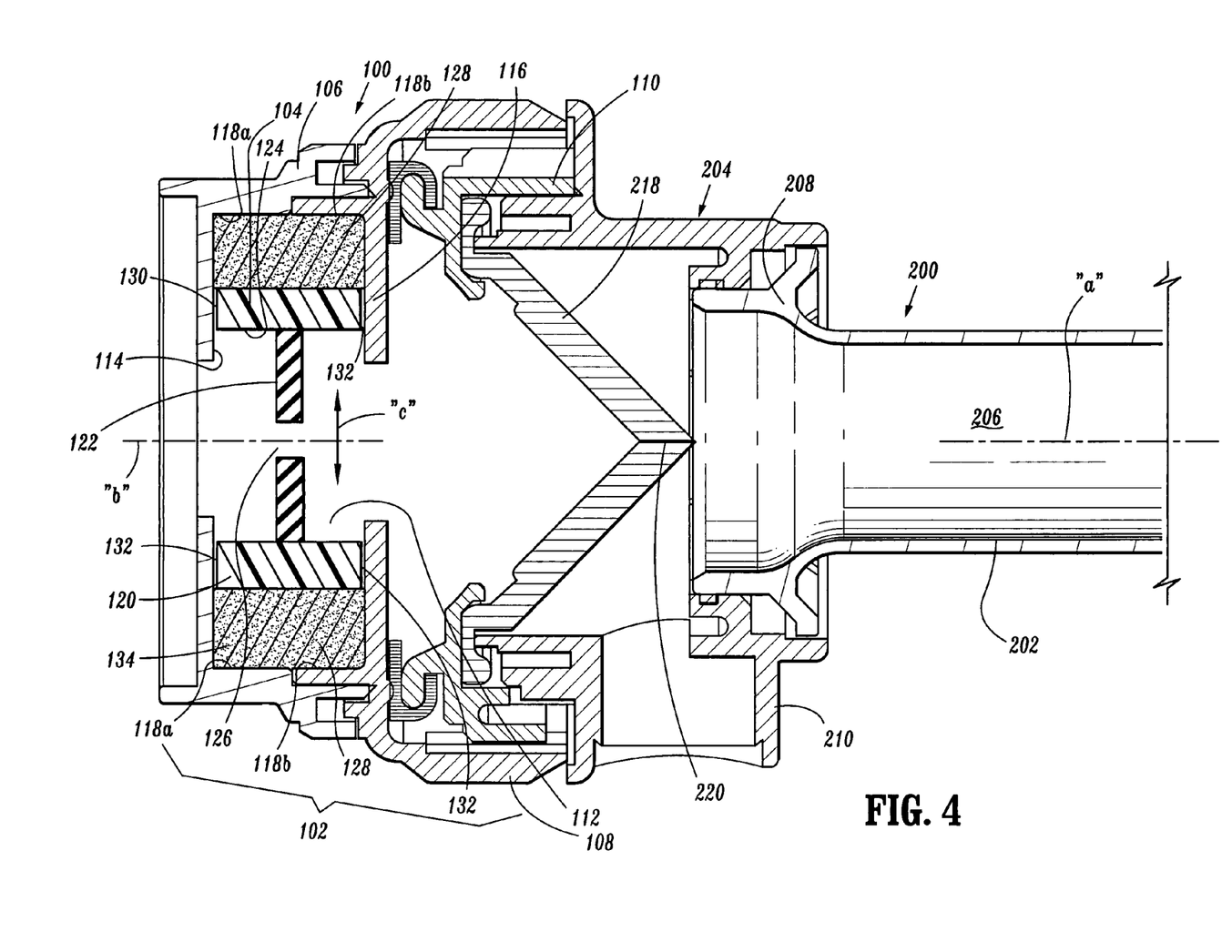
FIG. 4 is a side cross-sectional view of the cannula and seal assemblies in accordance with the embodiment of FIGS. 1-3.

Cannula housing 204 includes two components, specifically, housing flange 208 which is attached to the proximal end of cannula sleeve 202 and main housing 210 as shown in FIGS. 3-4. Main housing 210 is connectable to housing flange 208 through a bayonet coupling consisting of radially spaced tongues 212 on the exterior of housing flange 208 and corresponding recesses 214 within the interior of main housing 210, which are arranged to receive the tongues 212. Thereafter, housing flange 208 and main housing 210 are rotated to securely lock the tongues 212 within the recesses 214. Other conventional means, e.g., a threaded connection, snap fit, ultrasonic welding or any other means envisioned by one skilled in the art including, e.g., adhesive means, may be utilized to connect housing flange 208 and main housing 210. Main housing 210 further includes diametrically opposed housing grips 216 dimensioned and arranged for gripping engagement by the fingers of the user. Additionally or alternatively, suture anchors may extend from main housing 210. Although shown and described as two components, cannula housing 204 may be a single component and attached to cannula sleeve 202 by any of the aforementioned means. The housing flange 208, or the housing flange 208 and main housing 210, may be integrally formed with cannula sleeve 202.

With reference to FIG. 3, in conjunction with FIGS. 1-2, cannula housing 204 further includes valve 218. Valve 218 may be a zero-closure valve such as duck-bill valve having a slit 220 which is adapted to close in the absence of a surgical object and/or in response to insufflation gases of the pressurized cavity. In the alternative, valve 218 may be a gel seal, balloon valve, or a flapper valve.

Referring now to FIGS. 3-4, in conjunction with FIGS. 1-2, seal assembly 100 will be discussed in detail. Seal assembly 100 includes seal housing, generally identified as reference numeral 102, and seal 104 which is disposed within the seal housing 102. Seal housing 102 houses the sealing components of the assembly and defines the outer valve or seal body of the seal assembly 100. Seal housing 102 defines central seal housing axis "b" which is preferably parallel to the axis "a" of cannula sleeve 202 and, more specifically, coincident with the axis "a" of the cannula. Seal housing 102 incorporates three housing components, namely, first, second and third housing components 106, 108, 110, respectively, which, when assembled together, form the seal housing 102. Assembly of housing components 106, 108, 110 may be effected by any of the aforementioned connection means discussed with respect to cannula housing 204. Although shown and described as three components, it is appreciated that seal housing 102 may be a single component having the seal 104 mounted therein. In the assembled condition of housing components 106, 108, 110, an internal channel 112 is defined between upper and lower walls 114, 116 and side walls 118a, 118b. Internal channel 112 houses seal 104. Specifically, first component 106 has upper wall 114 which extends inwardly toward axis "b" from side wall 118a of the first component 106. Second component 108 has lower wall 116 which extends inwardly toward axis "b" from the side wall 118b of the second component 108.

With particular reference to FIGS. 3-4, seal 104 will be discussed in detail. Seal 104 includes annular support collar 120 and seal element 122 which is mounted within, or attached to, the support collar 120. Support collar 120 defines inner annular wall 124. Annular wall 124 has a height preferably slightly less than the height of internal chamber 112 to form a close tolerance with the upper and lower walls 114,116 defining the internal chamber 112. Support collar 120 is adapted to reciprocally slide in the direction of directional arrows "c" within internal chamber 112 in general transverse relation to axis "b". Support collar 120 may comprise a plastic, metallic or elastomer material and may be monolithically formed with seal element 122. Support collar 120 may comprise a two-part ring assembly such as the assembly disclosed in certain embodiments of commonly assigned U.S. Pat. No. 6,702,787, the disclosure of which is hereby incorporated by reference herein. The ring members have holes and posts that are arranged for mating with one another, joining the ring members together with the seal element fixed therebetween.

Seal element 122 is preferably a septum seal including an inner area defining a central aperture 126 for sealed reception of a surgical instrument. The periphery of seal element 122 is preferably secured to, or within, support collar 120. Consequently, seal element 122 moves with support collar 120 during manipulation of the inserted object. Any means for securing seal element 122 to support collar 120 are envisioned including with the use of cements, adhesives, etc. Seal element 122 may comprises an elastomeric material and may, or may not, include a fabric layer juxtaposed with the elastomeric material. For example, in one embodiment, seal element 122 desirably comprises an elastomeric material compression-molded with a fabric material such as disclosed in certain embodiments of the aforementioned U.S. Pat. No. 6,702,787, the entire disclosure of which is hereby incorporated by reference herein. The fabric may comprise a woven, knitted, braided, or non-woven material of polymeric materials. Alternatively, seal element 122 may comprise a gel material fabricated from soft urethane gel, silicon gel, etc. As noted above, seal element 122 and support collar 120 may be monolithically formed as a single unit. In a further embodiment, seal element 122 and the collar 120 may be formed of one or more elastomers. With seal 104 disposed in internal channel 112, an outer annular space 128 is defined in seal housing 102 about support collar 120. In addition, a gap 130 is defined between support collar 120 and upper wall 114 and a gap 132 is defined between support collar 120 and lower wall 116.

Seal 104 further includes a foam material 134 which is disposed within seal housing 102. Specifically, foam material 134 is disposed within annular space 128 surrounding support collar 120 and is generally contained within the space 128 by internal walls 114, 116, 118a, 118b and the support collar 120. The preferred foam material 134 is an open-cell foam material and preferably defines a donut or generally annular shape to correspond to the configuration of annular space 128. In one preferred embodiment, foam material 134 is at least partially saturated with a fluid such as a pharmacological, therapeutic or lubricious fluid or agent. Such pharmacological and therapeutic fluids are inclusive of, e.g., wound treatment agents, antibiotics, antiseptics, growth factors, anti-inflammatory agents, etc. Examples of lubricious fluids and agents include saline or silicone-based products.

The preferred fluid has a viscous quality or characteristic so as to substantially remain in annular space 128 for the duration of the surgical procedure. In this regard, the fluid fills gaps 130, 132 defined between support collar 120 and upper and lower walls 114,116 and forms a seal within each of these gaps 130,132 thereby preventing the escape of insufflation gases beyond the support collar 120.

Preferred fluids include saline solutions of hyaluronic acid, carboxymethyl cellulose, combinations and mixtures thereof, and fluids containing the foregoing. These fluids have been shown to decrease the formation of scarring and are commercially available from Genzyme Corporation.

Water and/or saline soluble materials which could be used include hyaluronic acid, celluloses, carboxymethyl celluloses (of various substitutions), methylcellulose, hydroxymethyl cellulose, hydroxypropyl cellulose, dextran, amino dextran, sulfonated dextran, carboxylated dextran, alginates (of various mannuronic and guluronic residues), chitosans (of various deactylations), polyphospholipids (MPC), polyvinyl pyrrolidone (PVP), polymethacrylic acids (PMAAs), polyacrylic acids (PAAs), polyhydroxyethylmethacrylates (PHEMAs), potassium sulfopropyl acrylates and methacrylates (KSPA and KSPMA), sulfonated styrenes (PS sulfonic acid), hydrophilic vinyl copolymers of above, polyacrylamides (PAM), polyamines, polyethylene glycols (PEGs), polypropylene glycols (PPGs), and copolymers of (Pluronics or Poloxamers), water soluble silicon copolymers, emulsions, etc., polyamino acids (i.e, polylysine), grafted polyamides, polysaccharides, lipids, polyorthoesters (POEs), polyorthoester-polyethylene glycol copolymers, polyethylene-styrene copolymers, and above of various molecular weight, architecture, viscosity, thermal properties, ratios, blends, grafts, copolymers, plasticizing oligomers, solubilities, electrical/insulative properties, viscosities and shear dependencies/rheologies, etc. Mixtures and combinations of the foregoing may be used, as well as other materials containing the foregoing.

When a lubricious material is incorporated within the foam material 134, the material also provides a lubricious coating on the surfaces of support collar 120 and upper and lower walls 114, 116 of housing 102 to thereby facilitate sliding movement of the support collar 120 along the upper and lower walls 114,116 and within the internal chamber 112. When a pharmacological agent or therapeutic agent is incorporated into the foam material 134, it is desirous to have some of the fluid seep through the small gaps 130, 132 and enter the internal area of seal housing 102. As appreciated, this fluid would eventually communicate through proximal component 106 of through cannula sleeve 202 of cannula assembly 200 and enter the tissue site to provide the desired therapeutic effect to the tissue site. This activity will be discussed in greater detail hereinbelow.

It is appreciated that the foam material 134 may incorporate both a lubricant and a therapeutic or pharmacological agent. It is also to be appreciated that therapeutic or pharmacological agents may also have a lubricious characteristic. In addition, foam material 134 with the contained fluid also serves to align support collar 120 and seal element 122 in a position in general alignment with the housing axis "b", i.e., the foam material 134 when in a state of equilibrium within the internal chamber 112, normally positions the support collar 120 and the seal element 122 in a position in general alignment with the seal axis "b".

Figure 5:
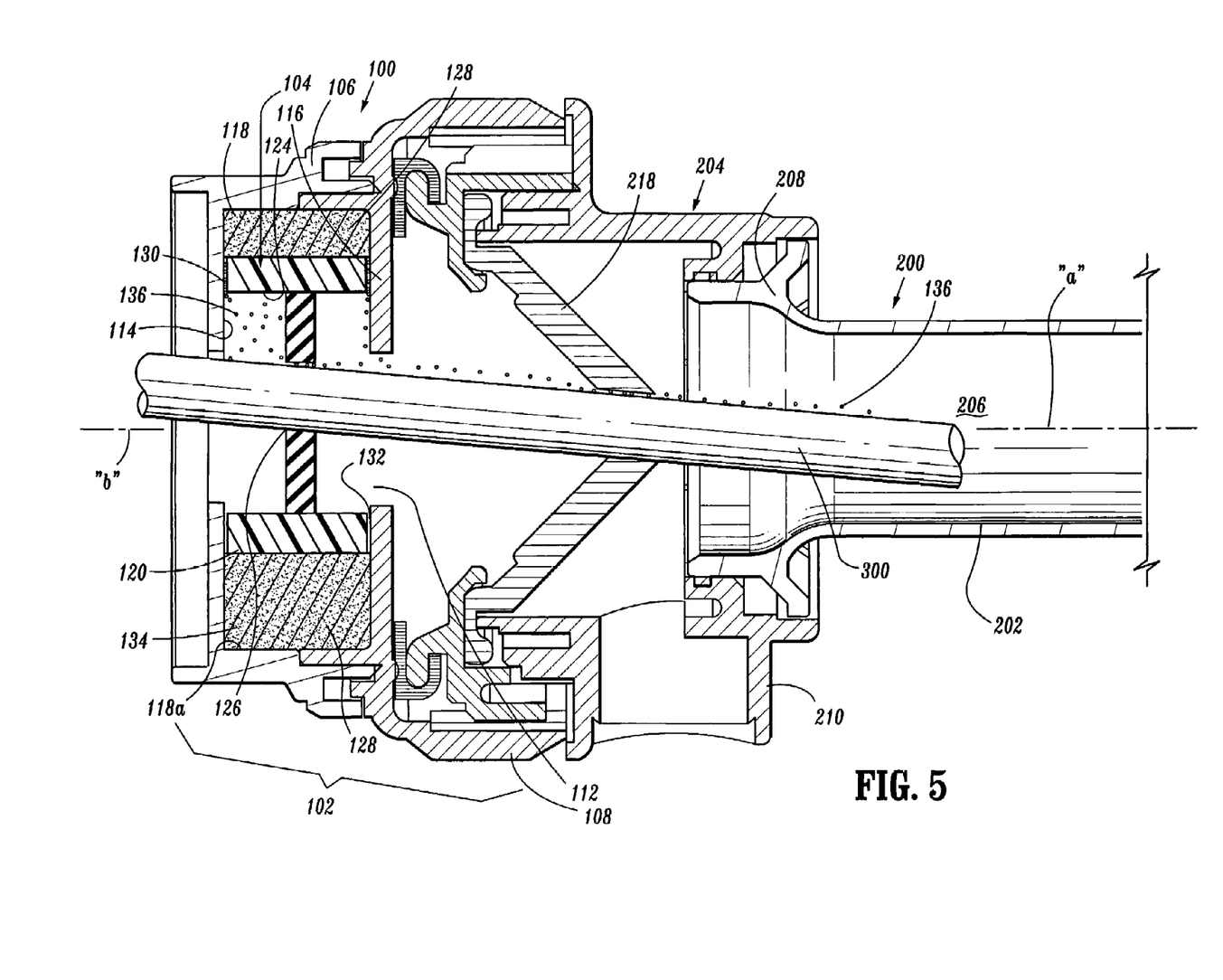
FIG. 5 is a side cross-sectional view similar to the view of FIG. 4 illustrating introduction and manipulation of a surgical instrument within the cannula and seal assemblies in accordance with the embodiment of FIGS. 1-4.

Seal assembly 100 may be associated with, or joined to, cannula assembly 200 in a variety of ways. In a preferred embodiment, seal housing 102 of seal assembly 100 and cannula housing 204 of cannula assembly 200 are adapted to detachably engage each other, e.g., through a bayonet lock, threaded attachment, latching attachment, or like mechanical means. In further embodiments, cannula housing 204 and valve 218 may be omitted and seal assembly 100 may be removably or permanently attached to flange 206. The seal assembly may be mounted to cannula assembly 100 before during or after application of the cannula assembly within the operative site. Alternatively, the seal assembly 100 may be built within cannula housing 204 as depicted in FIG. 5. As a further alternative, seal assembly 100 may be incorporated within a housing of a hand access device utilized in hand-assisted laparoscopic procedures.

The use of the seal assembly 100 and cannula assembly 200 in connection with introduction of a surgical instrument will be discussed. Seal assembly 100 is mounted to cannula assembly 200 and the cannula assembly 200 is introduced into an insufflated abdominal cavity typically utilizing a sharp or non-blade trocar obturator. With reference to FIG. 5, an object, e.g., an instrument 300 is inserted into seal assembly 100 through seal 104 whereby the portions defining the aperture 126 of seal element 122 stretch to accommodate the instrument 300 in substantial sealed relation therewith. The instrument 300 is distally passed through the valve 218 and into the body cavity to perform the desired procedure. During manipulation of the instrument, seal 104 traverses internal chamber 112 of seal housing 102. As noted above, the lubricious quality of the fluid contained by the foam material 134 facilitates movement of support collar 120 along upper and lower walls 114,116. In addition, upon movement of the instrument and support collar 120, the support collar 120 may compress the foam material 134 thereby causing some of the fluid, identified by reference numeral 136, to seep through gaps 130,132 and into the internal areas of the seal housing 102. This fluid 136 may be conveyed via the surgical instrument to the operative site to provide a therapeutic affect on the tissue site. The fluid 136 also desirably seeps through gaps 130,132 and out the proximal component 106 to the incision, providing moisture and/or other pharmacologic benefits to the site of the incision.

Figure 6:
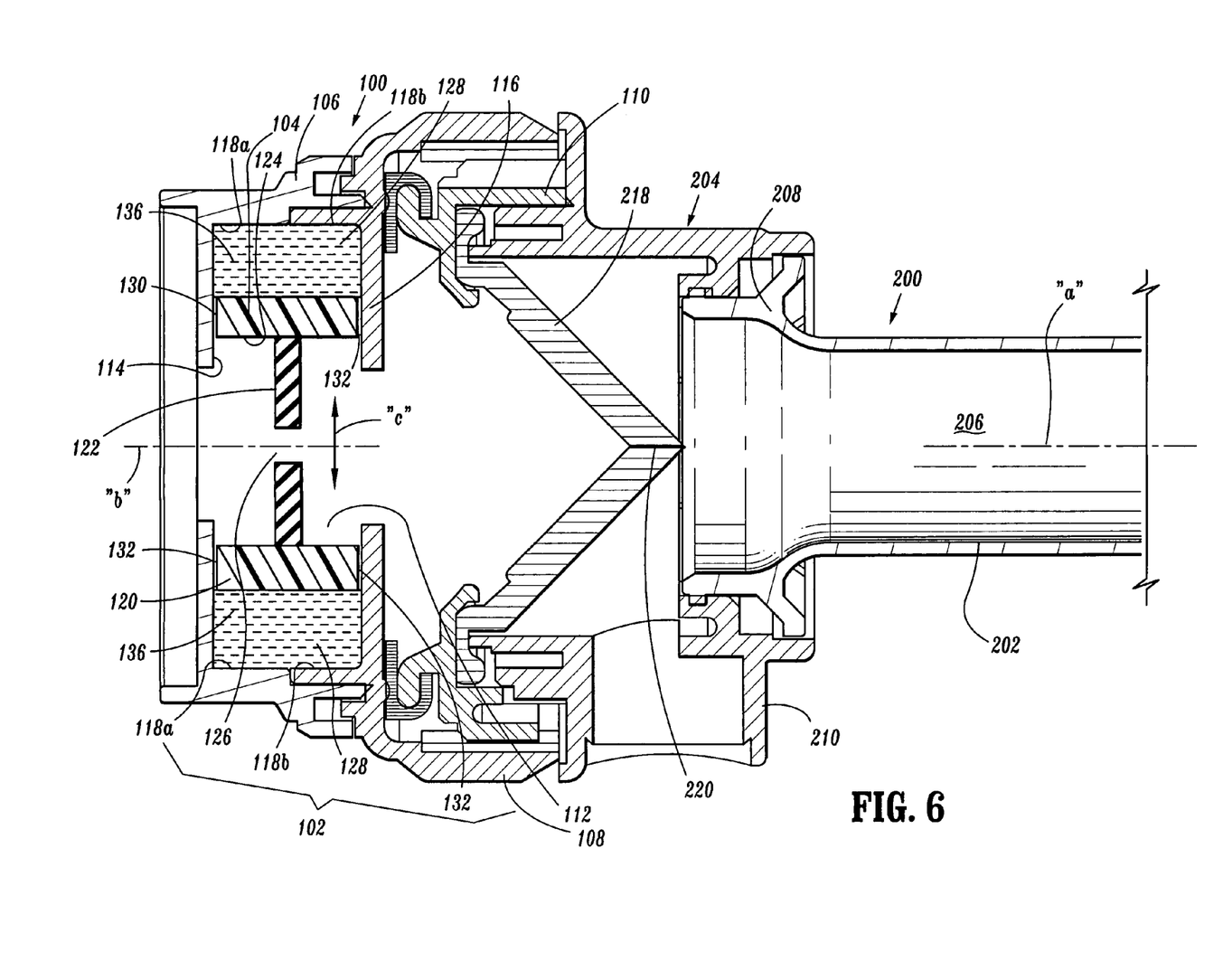
FIG. 6 is a schematic side cross-sectional view of an alternative embodiment of the seal assembly.

FIG. 6 illustrates another embodiment of the seal assembly 100 where the foam material 134 is eliminated. In accordance with this embodiment, fluid 136 is disposed within annular space 128 surrounding support collar 120. As discussed hereinabove, fluid 136 may be a therapeutic, pharmacological or lubricious agent or any other agent referred to above. Fluid 136 is preferably viscous such that the close tolerances at gaps 130,132 allow only some of the fluid 136 to exit from seal housing 102 to treat the underlying tissue as discussed hereinabove. The viscosity of the fluid 136 also serves to seal gaps 130,132. The fluid 134 may comprise a liquid or gaseous material and desirably has a therapeutic effect on the external and internal tissue sites. The fluid 136, although shown in FIG. 6 as filling the annular space 128, may partially fill the space 128, or coat the support collar 120 or surfaces of the seal housing 102.

While the invention has been particularly shown, and described with reference to the preferred embodiments, it will be understood by those skilled in the art that various modifications and changes in form and detail may be made therein without departing from the scope and spirit of the invention. For example, it is envisioned that seal element 104 may be fixed within seal housing 102 without any traversing movement within internal chamber 112. In another example, the seal element may be shaped so as to engage the housing. In a further example, the seal element may or may not be secured to a support collar or other mounting.

Seal element 104 may include seals of various shapes and constructions, such as a flat disc-shaped, conical, or hour-glass-shaped member including a fabric material molded with an elastomer. The seals disclosed in certain embodiments of U.S. patent application Ser. No. 10/165,133, filed Jun. 6, 2002, the disclosure of which is hereby incorporated by reference, may be used. In a further alternative, seal element 104 is preferably a fabric seal and is desirably arranged so as to have a constriction. For example, seal element 104 may have the general shape of an hourglass. The fabric can be a woven material, a braided material, or a knitted material. The type of material is selected to provide a desired expansiveness. For example, a braid of varying end count and angle may be selected. A preferred material is a synthetic material such as nylon, Kevlar (Trademark of E.I. DuPont de Nemours and Company) or any other material that will expand and compress about an instrument inserted therethrough. The selected material desirably minimizes or prevents the formation of gaps when the instrument is introduced into seal element 104. The material of seal element 104 may be porous or impermeable to the insufflation gas. If porous, seal element 104 may include a coating of a material which is impermeable to the insufflation gas or at least a portion of the valve may be coated. In addition, the fabric may be coated on its interior with urethane, silicon or other flexible lubricious materials to facilitate passage of an instrument or other object, such as the hand and arm, through the seal element 104. In certain embodiments, the fabric is twisted about the axis "a" so as to form a constriction or closed portion. The fabric is desirably constructed of a material and/or arranged so that the fabric forms a constriction or closure. The seal element 104 may also be molded so as to have a constriction or may be knitted, braided or woven so as to have a constriction. Other arrangements for seal element 104 are also envisioned. Accordingly, modifications such as those suggested above, but not limited thereto, are to be considered within the scope of the invention.

What is claimed is:

1. A seal assembly for use with a surgical access apparatus, which comprises:
   a housing defining a longitudinal axis and having a passageway dimensioned to permit passage of an object, the housing adapted for mounting to a surgical access apparatus and having internal wall portions;
   a seal being mounted within the housing, the seal including an outer annular support collar and an inner seal portion, the inner seal portion adapted to form a substantial sealing relation with the object, the seal being mounted for reciprocal movement in a general transverse direction to the longitudinal axis, the support collar and internal wall portions of the housing defining an internal chamber therebetween; and
   a viscous fluid within the internal chamber externally of, and surrounding, the seal and in contact with the internal wall portions, the viscous fluid cooperating with the internal wall portions to form a substantial seal between the seal and the housing;
   wherein the outer annular support collar of the seal and the internal wall portions of the housing define at least one gap therebetween to permit seepage of the fluid from the internal chamber into the passageway.

2. The seal assembly according to claim 1 wherein the fluid has a lubricious characteristic to facilitate sliding movement of the annular support collar relative to the internal wall portions of the housing.

3. The seal assembly according to claim 2 wherein the fluid comprises a lubricant.

4. The seal assembly according to claim 1 wherein the fluid comprises a therapeutic agent or a pharmacological agent.

5. The seal assembly according to claim 4 wherein the fluid comprises a medicinal, wound treatment agent, antibiotic, antiseptic, growth factor or an anti-inflammatory agent.

6. The seal assembly according to claim 1 further comprising a foam material within the internal chamber wherein the fluid is disposed within the foam material.

7. A surgical access apparatus, which comprises:
   a housing member having internal wall portions;

an access member mounted to the housing member, the access member defining a central longitudinal axis and having a longitudinal opening dimensioned for passage of an object;

a seal member disposed within the housing member and adapted to traverse the housing member upon manipulation of the object, the seal member including a peripheral portion and an inner seal portion, the inner seal portion adapted to permit passage of the object in substantial sealed relation therewith, the peripheral portion of the seal member and the internal wall portions of the housing member defining an internal chamber therebetween; and a foam material within the internal chamber externally of and surrounding the peripheral portion of the seal member, the foam material comprising a viscous fluid in direct contact with the internal wall portions of the housing member and being adapted to form a fluid tight seal between the peripheral portion of the seal member and the internal wall portions of the housing;

wherein the housing member and the seal member are dimensioned and configured to define at least one gap between the internal wall portions and the seal member whereby during manipulation of the object the fluid communicated from the internal chamber into the longitudinal opening of the access member.

8. The surgical access apparatus according to claim 7 wherein the foam material comprises a lubricant to facilitate sliding movement of the peripheral portion of the seal member relative to the internal wall portions of the housing.

9. The surgical access apparatus according to claim 7 wherein the foam material includes a pharmacological agent or a therapeutic agent.

10. The surgical access apparatus according to claim 7 wherein the inner seal portion of the seal member includes a central aperture for reception of the object.

11. The surgical access apparatus according to claim 10 further including a zero closure valve, the zero closure valve adapted to close in the absence of the object.

12. The surgical access apparatus according to claim 7 wherein the housing is a cannula housing and the access member is a cannula sleeve.

13. The seal assembly according to claim 1 wherein the inner seal portion depends inwardly from the annular support collar in substantially orthogonal relation thereto.

14. The seal assembly according to claim 1 wherein the seal defines an aperture extending through the inner seal portion when the in a normal condition.

* * * * *

UNITED STATES PATENT AND TRADEMARK OFFICE
CERTIFICATE OF CORRECTION

| | | |
|---|---|---|
| PATENT NO. | : 7,608,082 B2 | Page 1 of 1 |
| APPLICATION NO. | : 11/030634 | |
| DATED | : October 27, 2009 | |
| INVENTOR(S) | : Cuevas et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 966 days.

Signed and Sealed this

Twelfth Day of October, 2010

David J. Kappos
*Director of the United States Patent and Trademark Office*